United States Patent
Fan et al.

(10) Patent No.: US 11,185,329 B2
(45) Date of Patent: Nov. 30, 2021

(54) OPERATING STRUCTURE OF SURGICAL CLIP APPLIER

(71) Applicant: APEX GLORY HOLDINGS LTD., Eden Island (SC)

(72) Inventors: Hong-Yang Fan, Zhudong Township (TW); Shih-Hao Huang, Zhudong Township (TW)

(73) Assignee: MEDSCOPE BIOTECH CO., LTD., Zhunan Town (TW)

( * ) Notice: Subject to any disclaimer, the term of this patent is extended or adjusted under 35 U.S.C. 154(b) by 439 days.

(21) Appl. No.: 16/493,974

(22) PCT Filed: Nov. 9, 2017

(86) PCT No.: PCT/SC2017/000008
§ 371 (c)(1),
(2) Date: Sep. 13, 2019

(87) PCT Pub. No.: WO2019/190364
PCT Pub. Date: Oct. 3, 2019

(65) Prior Publication Data
US 2021/0330329 A1    Oct. 28, 2021

(30) Foreign Application Priority Data

Nov. 10, 2016 (TW) ................... 105136729

(51) Int. Cl.
*A61B 17/10* (2006.01)
*A61B 17/00* (2006.01)

(52) U.S. Cl.
CPC .... *A61B 17/10* (2013.01); *A61B 2017/00367* (2013.01); *A61B 2017/00407* (2013.01)

(58) Field of Classification Search
CPC ..... A61B 17/10; A61B 17/115; A61B 17/128; A61B 17/068; A61B 2017/00367; A61B 2017/00407
See application file for complete search history.

(56) References Cited

U.S. PATENT DOCUMENTS

2019/0000482 A1* 1/2019 Hu .................. A61B 17/00234

* cited by examiner

*Primary Examiner* — Melanie R Tyson
*Assistant Examiner* — Mohammed S Adam
(74) *Attorney, Agent, or Firm* — Birch, Stewart, Kolasch & Birch, LLP

(57) ABSTRACT

An operating structure of a surgical clip applier is provided to drive a clip clamping unit. The operating structure of the surgical clip applier comprises: a body; a front driving element for driving the clip clamping unit; a restoring spring for driving the front driving element to move backward; a press-control element pivotally connected to the body; a front driving arm pivotally connected to the press-control element; and a lower driving arm with two ends pivotally connected to the body and the front driving arm, respectively, to drive the front driving element to move forward.

8 Claims, 10 Drawing Sheets

US 11,185,329 B2

OPERATING STRUCTURE OF SURGICAL CLIP APPLIER

BACKGROUND OF THE INVENTION

1. Technical Field

The present invention relates to medical equipment and, more particularly, to an operating structure of a surgical clip applier.

DESCRIPTION OF THE PRIOR ART

A conventional operating structure of a surgical clip applier is not only intricate but is also notorious for unstable transmission; as a result, not only is its position control imprecise, but its components are also susceptible to damage. Furthermore, when incompletely pressed, the conventional operating structure of a surgical clip applier fails to perform a clamping operation once, completely, compulsorily and smoothly.

Therefore, considering its aforesaid drawbacks, the conventional operating structure of a surgical clip applier still has room for improvement.

BRIEF SUMMARY OF THE INVENTION

In view of the aforesaid drawbacks of the prior art, it is an objective of the present invention to provide an operating structure of a surgical clip applier, which not only features enhanced transmission stability and precision but also performs a complete operation.

In order to achieve the above and other objectives, the present invention provides an operating structure of a surgical clip applier, for driving a clip clamping unit, the operating structure comprising: a body; a front driving element for driving the clip clamping unit; a restoring spring for driving the front driving element to move backward; a press-control element pivotally connected to the body; a front driving arm pivotally connected to the press-control element; and a lower driving arm with two ends pivotally connected to the body and the front driving arm, respectively, wherein the lower driving arm drives the front driving element to move forward.

Hence, the present invention features an association structure conducive to accurate, stable driving operation, thereby achieving the objectives of the present invention.

Preferably, the operating structure of a surgical clip applier further comprises a tooth positioning element pivotally connected to the lower driving arm. The tooth positioning element has a resilient arm with dogs. A compression spring presses against the lower driving arm and the tooth positioning element. The body has positioning teeth whereby the tooth positioning element is positioned in place.

Preferably, the body has an oblique protruding portion disposed beside the positioning teeth and a tooth escape recess disposed below the positioning teeth, whereas the tooth positioning element has a stud slidable into the tooth escape recess of the body through the oblique protruding portion, thereby achieving a complete operation.

Preferably, the operating structure of a surgical clip applier further comprises: a rear driving element for driving the clip clamping unit; a rear slider having a slide rod for driving the rear driving element; a rear driving arm pivotally connected to the press-control element and having an oblong hole which the slide rod of the rear slider is penetratingly disposed at to effectuate driving.

Preferably, the operating structure of a surgical clip applier further comprises a counting unit having a ratchet wheel, a wheel press-rotating element, and a reverse rotation preventing element. The ratchet wheel displays numerals. The wheel press-rotating element is pivotally disposed at and resiliently pressed against the press-control element once to drive the ratchet wheel to turn by one tooth's angle. The reverse rotation preventing element prevents reverse rotation of the ratchet wheel.

Preferably, the body has a spring-pressing portion, whereas the restoring spring fits between the front driving element and the spring-pressing portion of the body.

DETAILED DESCRIPTION OF THE INVENTION

Figure 1:
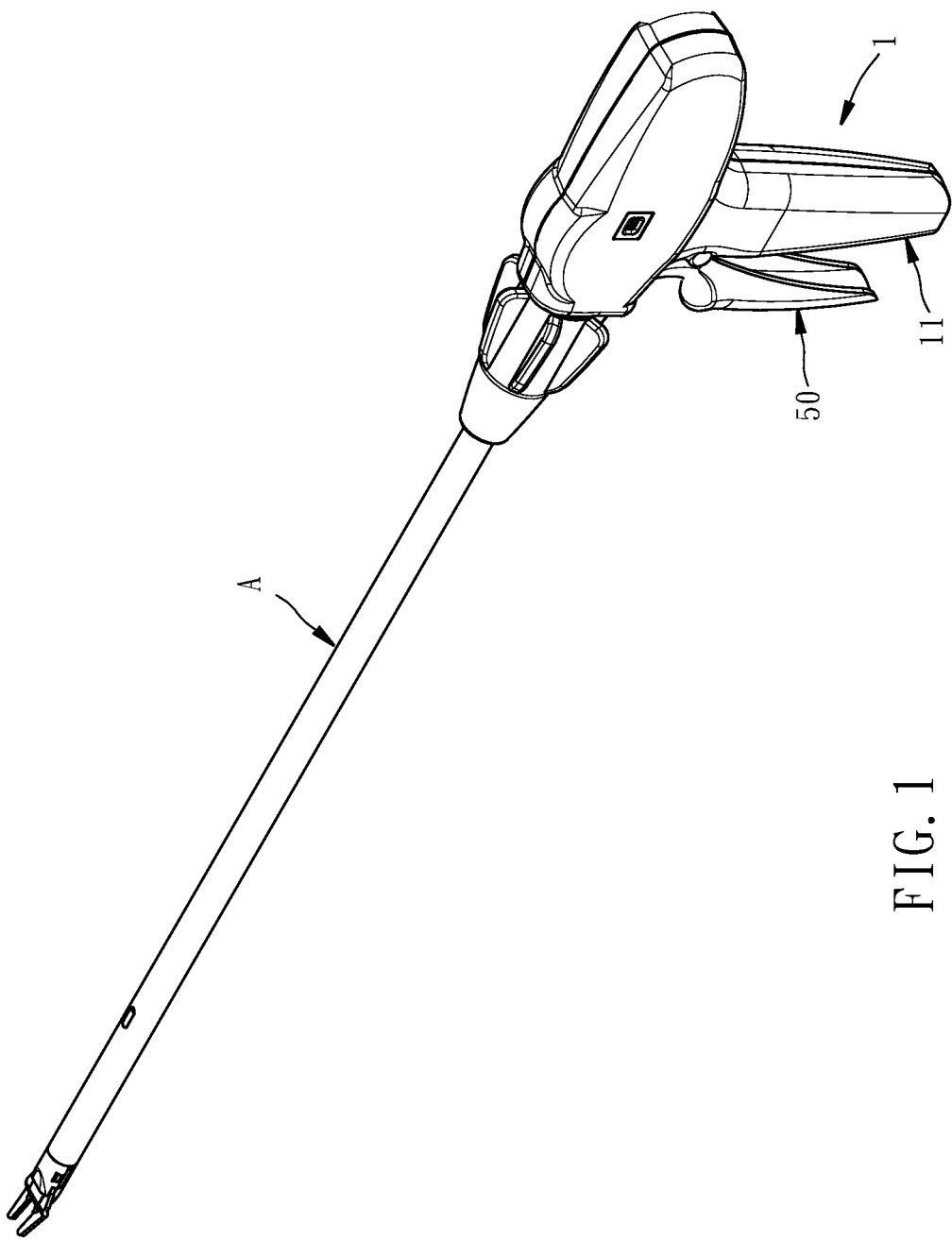
FIG. 1 is a perspective view of an operating structure of a surgical clip applier according to a preferred embodiment of the present invention.
Figure 2:
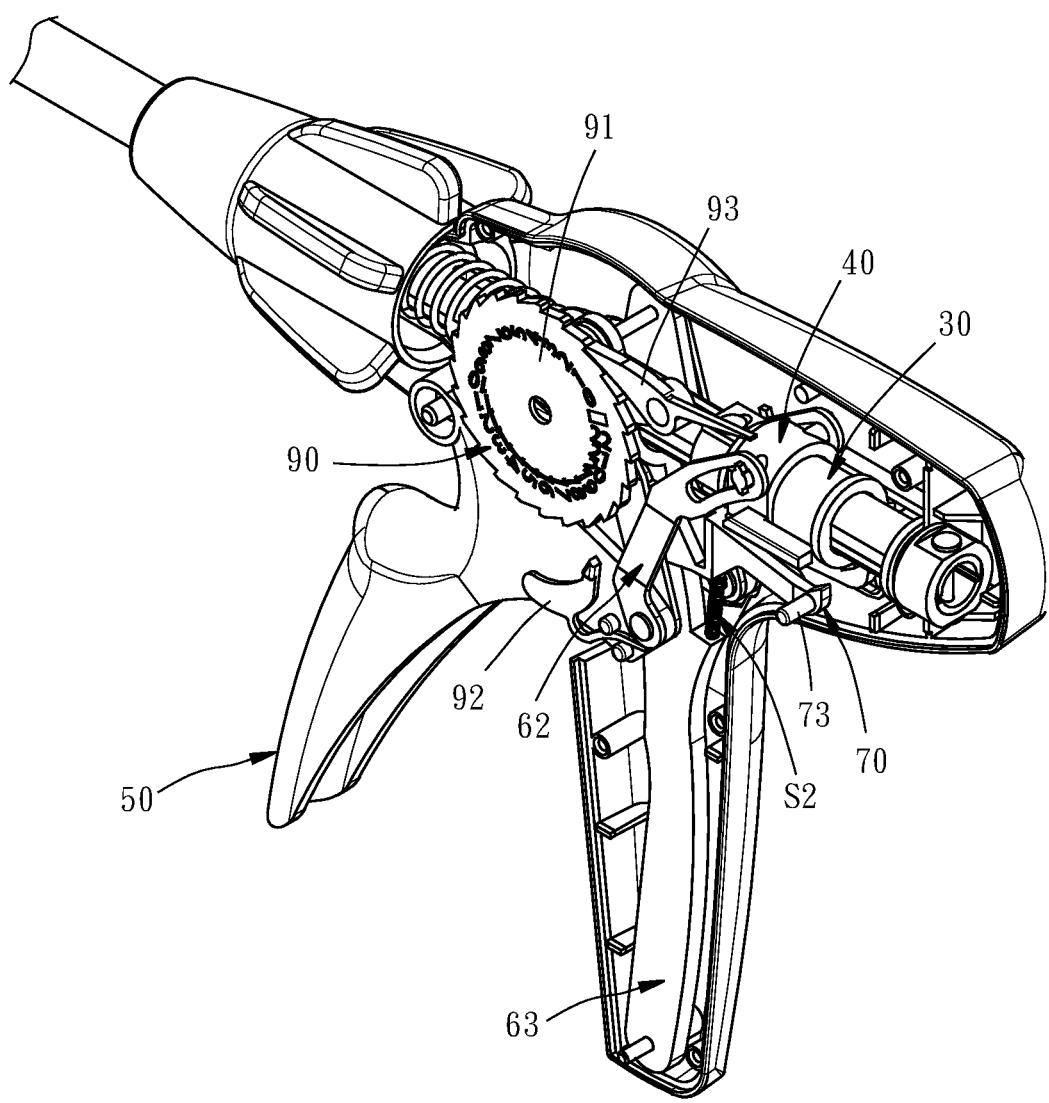
FIG. 2 is a perspective view of the operating structure of a surgical clip applier according to a preferred embodiment of the present invention but with a casing thereof removed.
Figure 3:
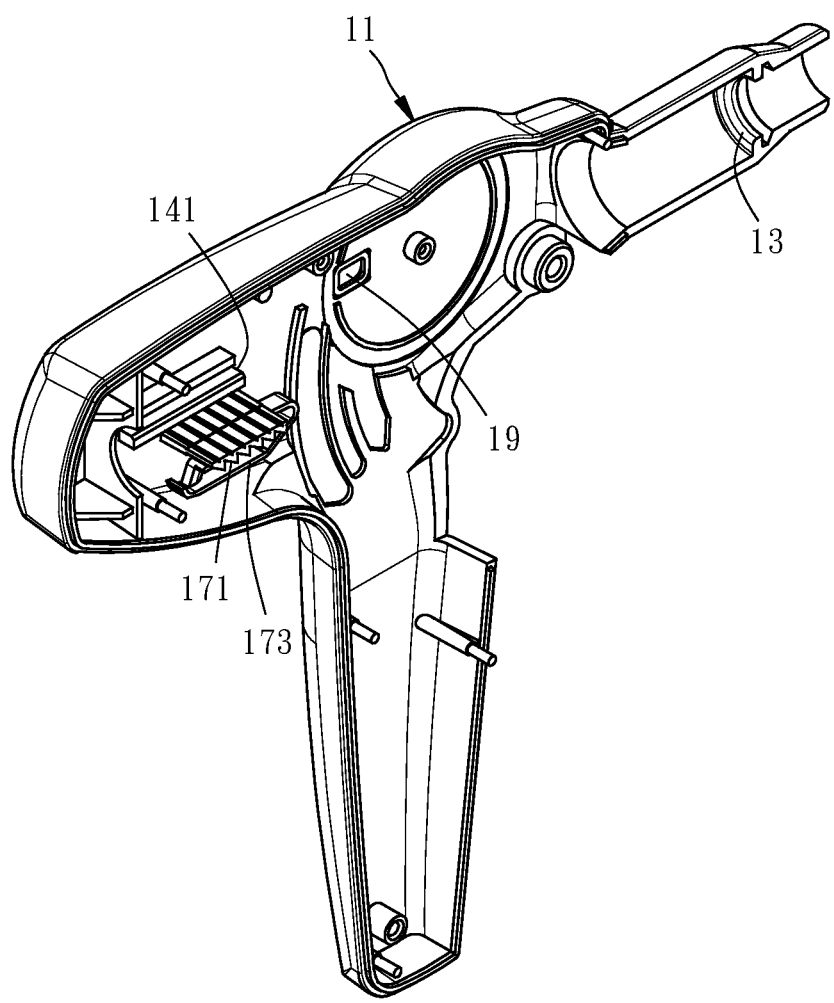
FIG. 3 is a perspective view of the casing according to a preferred embodiment of the present invention.
Figure 4:
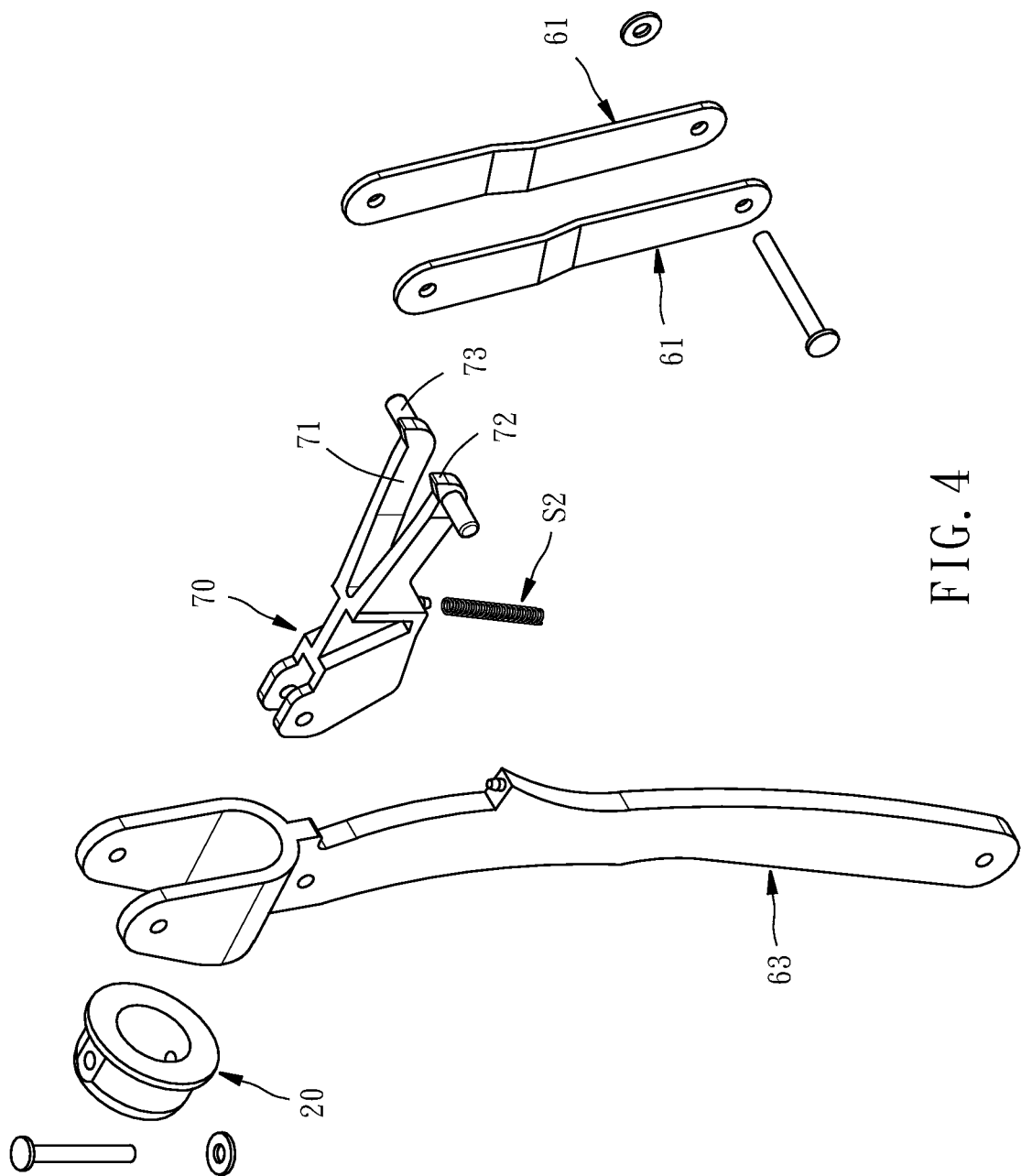
FIG. 4 is a partial perspective exploded view of the operating structure of a surgical clip applier according to a preferred embodiment of the present invention.
Figure 5:
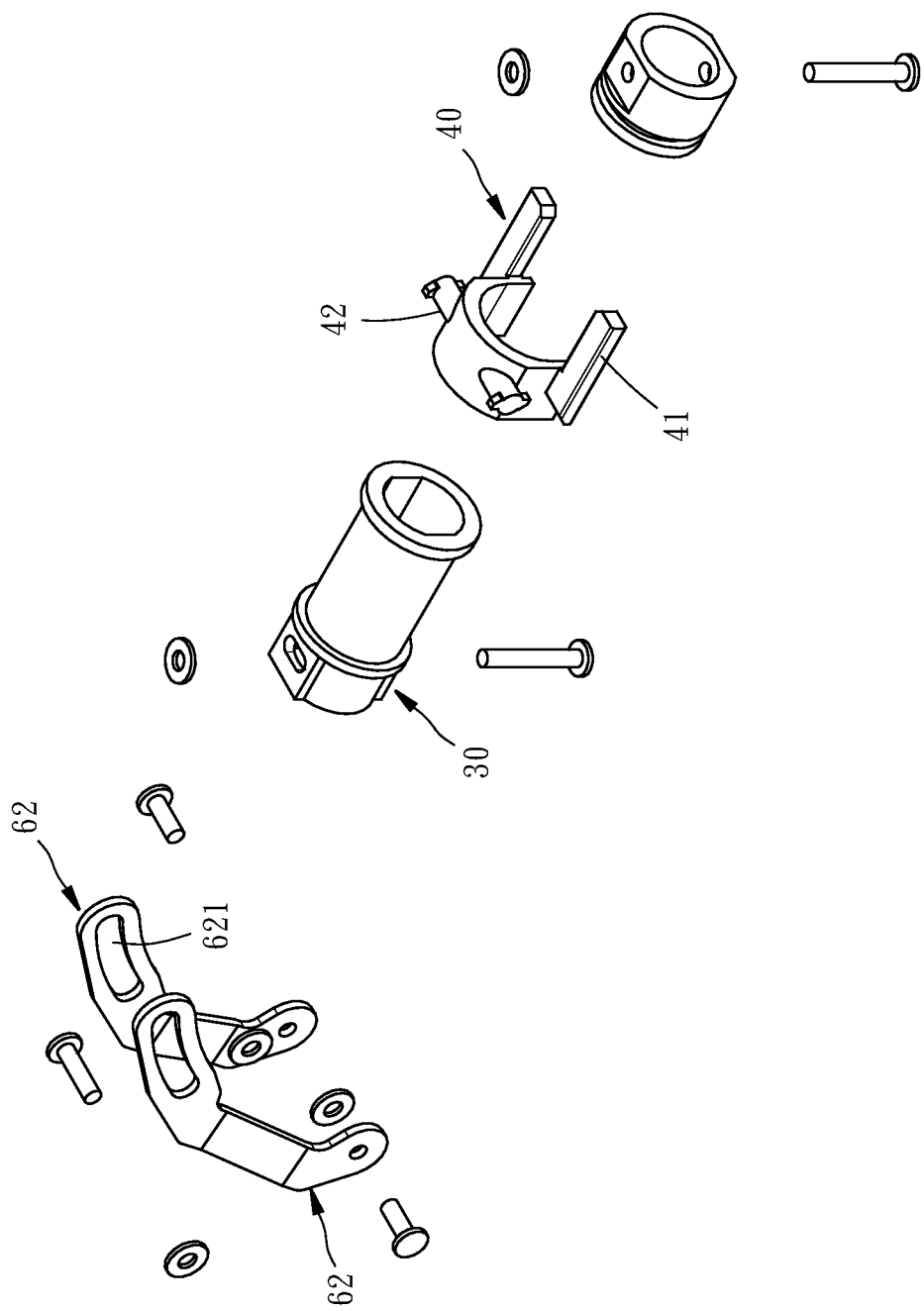
FIG. 5 another partial exploded view of the operating structure of a surgical clip applier according to a preferred embodiment of the present invention.
Figure 6:
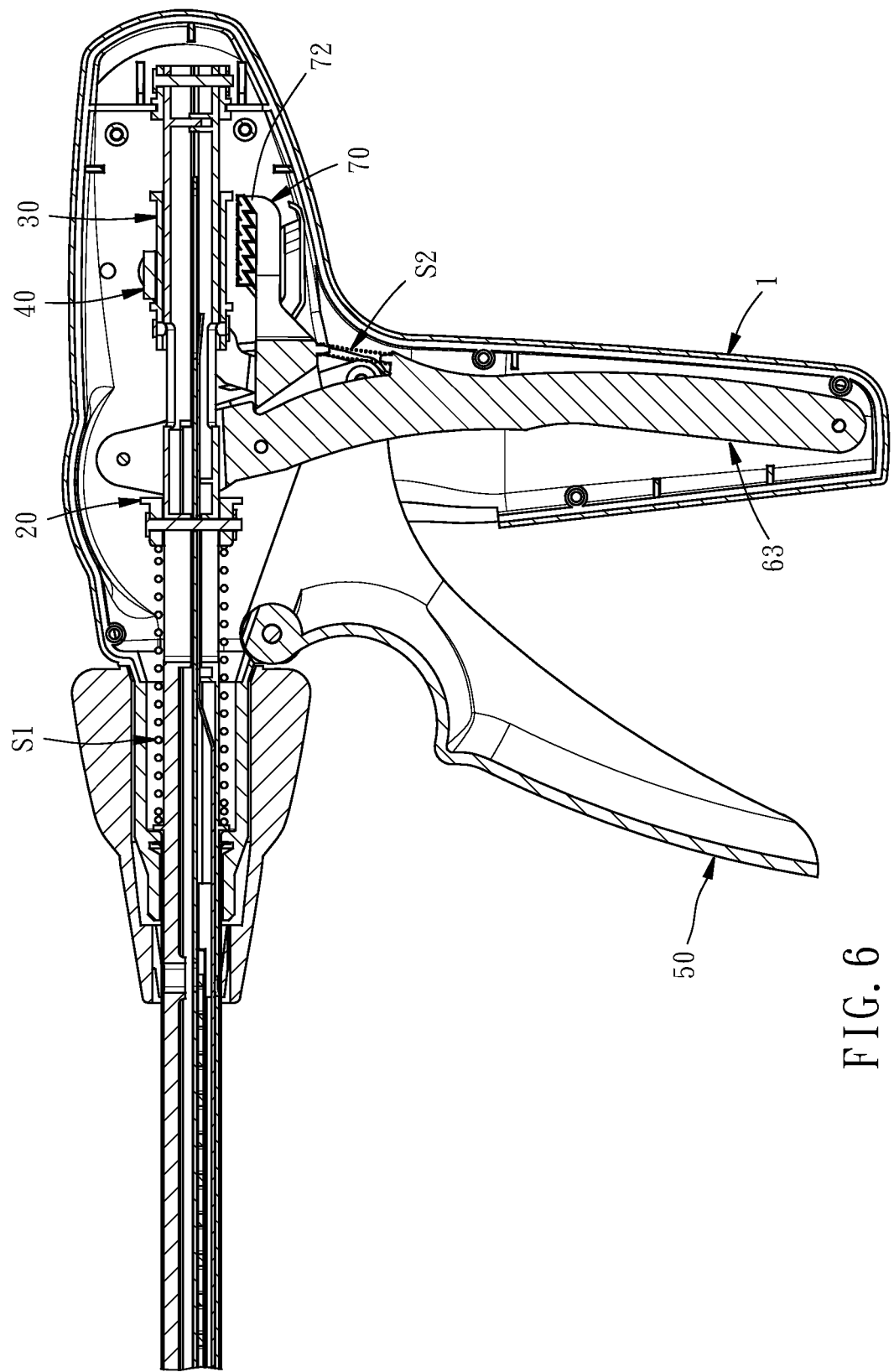
FIG. 6 is a cross-sectional view of the operating structure of a surgical clip applier according to a preferred embodiment of the present invention.

The present invention provides an operating structure of a surgical clip applier, which is described and illustrated by embodiments and diagrams below.

As shown in the diagrams, the operating structure of a surgical clip applier drives a clip clamping unit A.

The operating structure of a surgical clip applier comprises a body 1, a front driving element 20, a restoring spring S1, a rear driving element 30, a rear slider 40, a press-control element 50, two front driving arms 61, a lower driving arm 63, a tooth positioning element 70, and a counting unit 90.

The clip clamping unit A has one end pivotally disposed at the body 1. In this embodiment, the body 1 consists of two casings 11 couple together.

The body 1 has a spring-pressing portion 13, two slide grooves 141, two positioning teeth 171, two oblique protruding portions 172 disposed beside the positioning teeth 171, two tooth escape recesses 173 disposed below the positioning teeth 171, and a window 19 disposed at the casings 11.

The front driving element 20 drives the clip clamping unit A.

The body 1 has a spring-pressing portion 13. The restoring spring S1 fits between the front driving element 20 and the spring-pressing portion 13 of the body 1.

The restoring spring S1 drives the front driving element 20 to move backward.

The rear driving element 30 drives the clip clamping unit A.

The rear slider 40 has two slide blocks 41 and a slide rod 42. The two slide blocks 41 are slidably disposed at the slide grooves 141 of the body 1.

The press-control element 50 is pivotally connected to the body 1.

The two front driving arms 61 are pivotally connected to the press-control element 50.

Two rear driving arms 62 are pivotally connected to the press-control element 50. The rear driving arms 62 each have an oblong hole 621. The slide rod 42 of the rear slider 40 is penetratingly disposed at the oblong holes 621 to drive the rear driving arms 62.

The lower driving arm 63 has two ends pivotally connected to the body 1 and the front driving arms 61, respectively. The lower driving arm 63 drives the front driving element 20 to move forward.

The front driving arms 61, rear driving arms 62 and lower driving arm 63 are paired or grouped together to form a link rod unit.

The tooth positioning element 70 is pivotally connected to the lower driving arm 63. A compression spring S2 presses against the lower driving arm 63 and the tooth positioning element 70.

The tooth positioning element 70 has two resilient arms 71 each having two dogs 72 and two studs 73. The two dogs 72 are unidirectionally engaged with the positioning teeth 171 of the body 1 for positioning. The two studs 73 slide into the tooth escape recesses 173 of the body 1 through the oblique protruding portions 172.

The counting unit 90 has a ratchet wheel 91, a wheel press-rotating element 92, and a reverse rotation preventing element 93. The ratchet wheel 91 is rotatably disposed at the body 1 and displays numerals. The wheel press-rotating element 92 is pivotally disposed at and resiliently pressed against the press-control element 50 once to drive the ratchet wheel 91 to turn by one tooth's angle. The reverse rotation preventing element 93 is disposed at the body 1 to prevent reverse rotation of the ratchet wheel 91.

Figure 7:
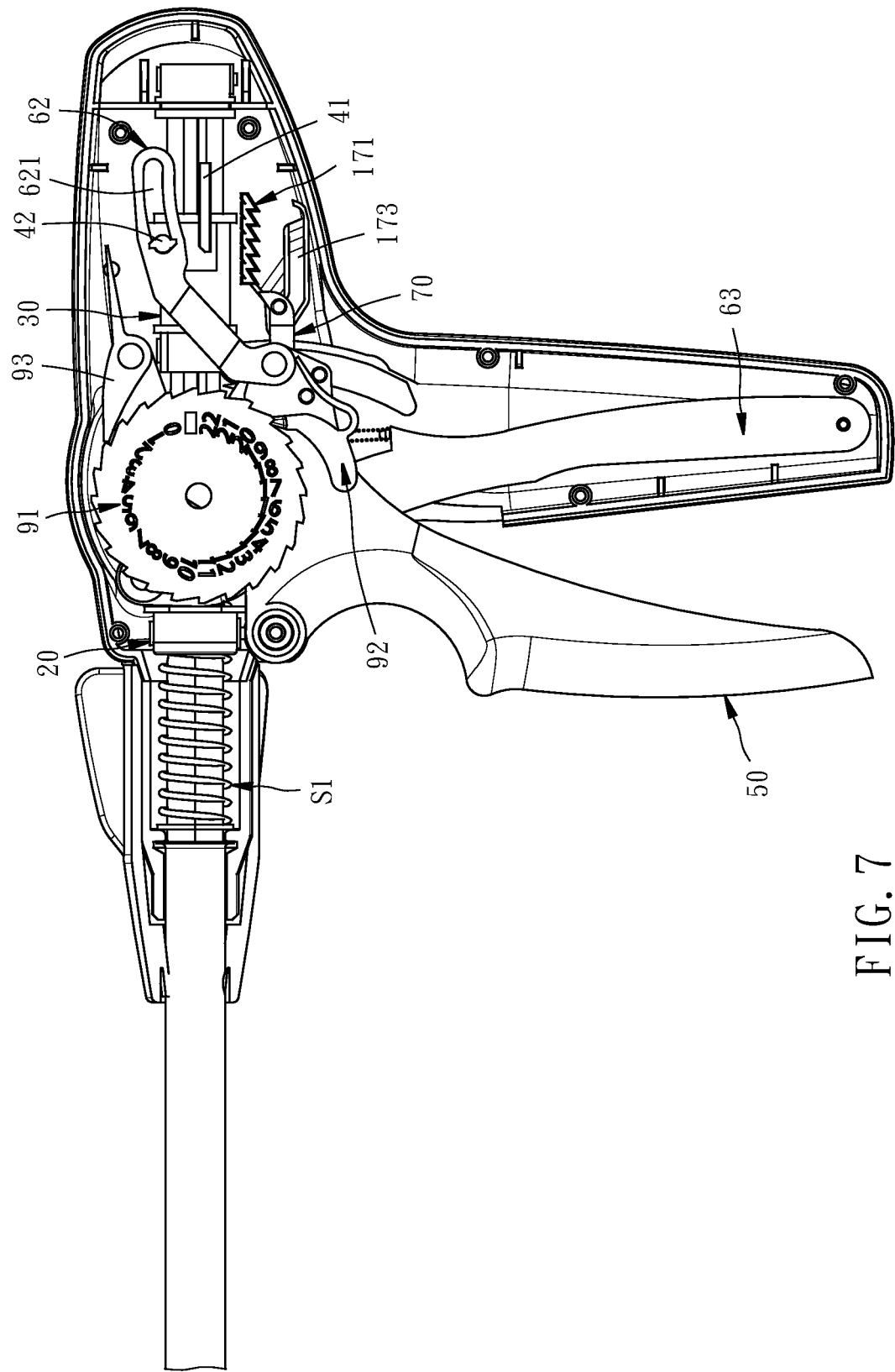
FIG. 7, which is similar to FIG. 6, shows another operating state of the operating structure of a surgical clip applier.

To operate the surgical clip applier, a user presses the press-control element 50 so that the press-control element 50 drives the front driving arms 61 and the rear driving arms 62, as shown in FIG. 7.

The front driving arms 61 drive the lower driving arm 63 to swing pivotally. The lower driving arm 63 drives the front driving element 20 to move forward. The front driving element 20 drives the components of the clip clamping unit A to move forward.

The rear driving arms 62 drive the rear slider 40 to move forward, and thus the rear slider 40 drives the rear driving element 30 to move forward. As a result, the rear driving element 30 drives the components of the clip clamping unit A to move forward.

The dogs 72 of the tooth positioning element 70 are unidirectionally engaged with the positioning teeth 171 of the body 1 for positioning, and in consequence the user can only keep pressing the press-control element 50 for operation.

When the user's press reaches its maximum limit, the rear driving element 30 enables a clip pusher of the clip clamping unit A to retract by moving it backward for a predetermined distance, whereas the front driving element 20 drives the clip clamping unit A to clamp its clip easily.

Figure 8:
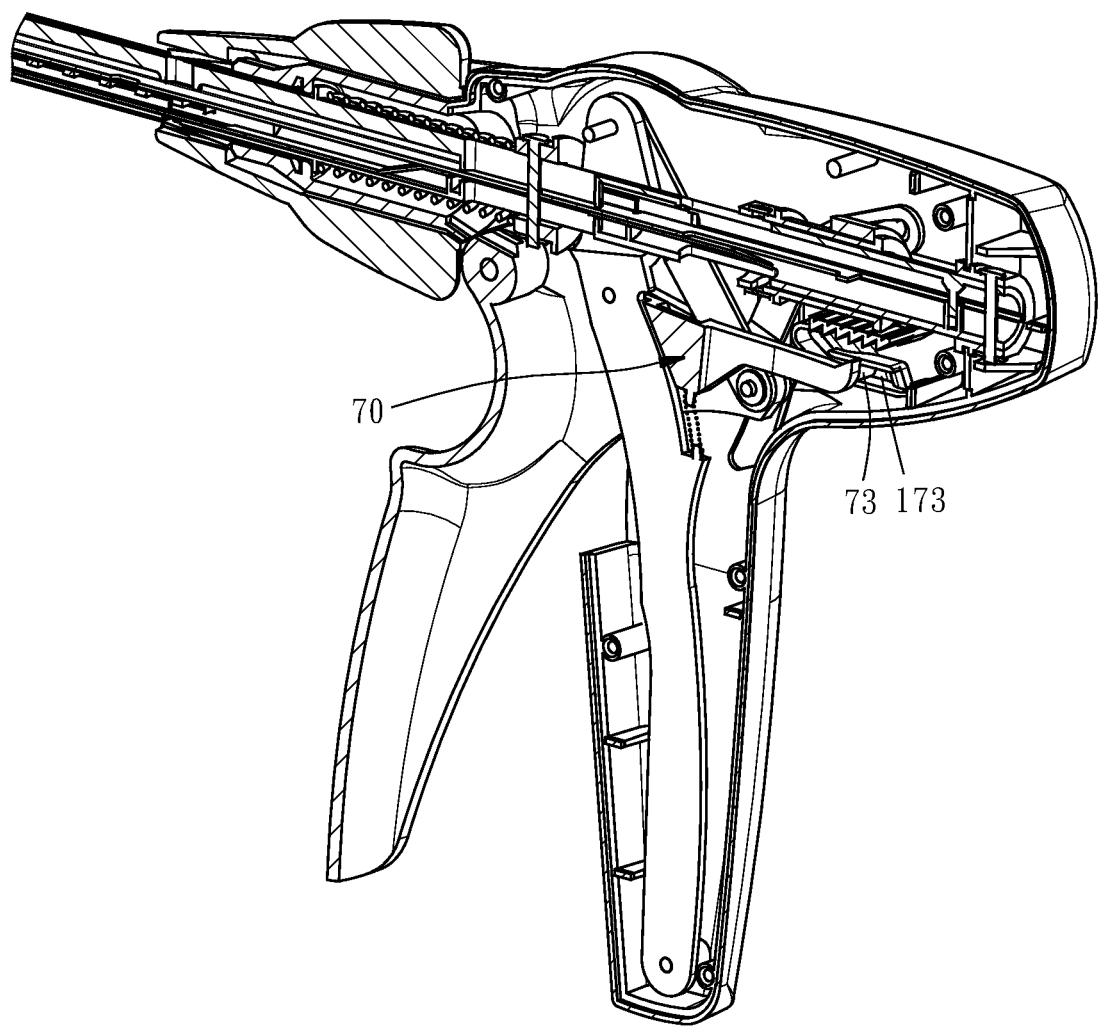
FIG. 8 is a cutaway view of another operating state of the operating structure of a surgical clip applier according to a preferred embodiment of the present invention.
Figure 9:
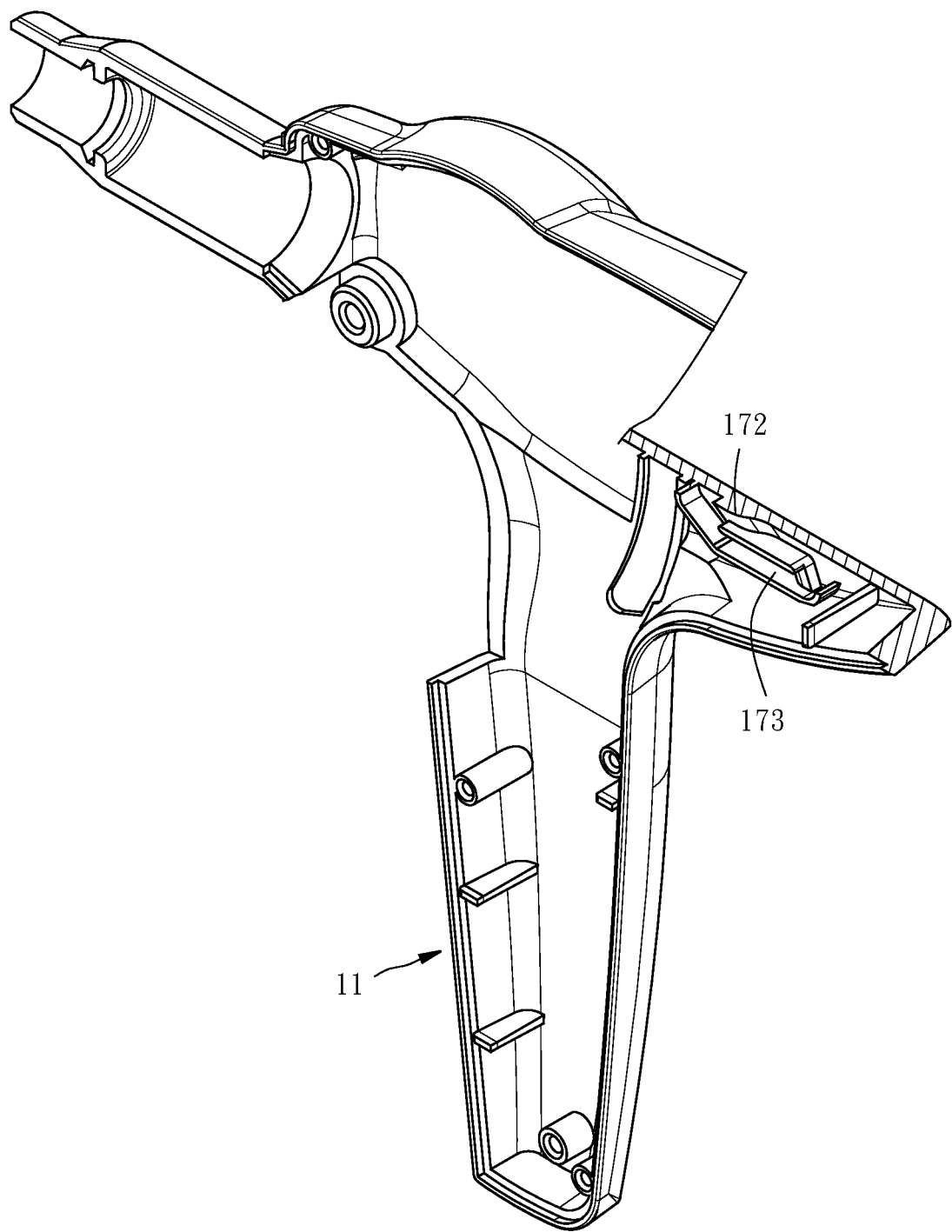
FIG. 9 is a cutaway view of the casing according to a preferred embodiment of the present invention.

Referring to FIG. 8, when the user releases the press-control element 50, the studs 73 of the tooth positioning element 70 pass the oblique protruding portions 172 and enter the tooth escape recesses 173 of the body 1. The tooth escape recesses 173 each have an oblique surface pressing against the studs 73 inward so that the studs 73 can only escape from the tooth escape recesses 173 from the other ends thereof, thereby restoring the studs 73 to its original, intact state.

Therefore, the operating structure of a surgical clip applier according to the present invention has a driving mechanism conducive to precise, satisfactory operation. Furthermore, the operating structure of a surgical clip applier according to the present invention is capable of exercising unidirectional control required for a complete operation.

The wheel press-rotating element 92 of the counting unit 90 operates in conjunction with the lower driving arm 63 to indicate precisely the number of clips in use.

As shown above, the embodiments of the present invention have the aforesaid advantages and thus achieve the objectives of the present invention.

Figure 10:
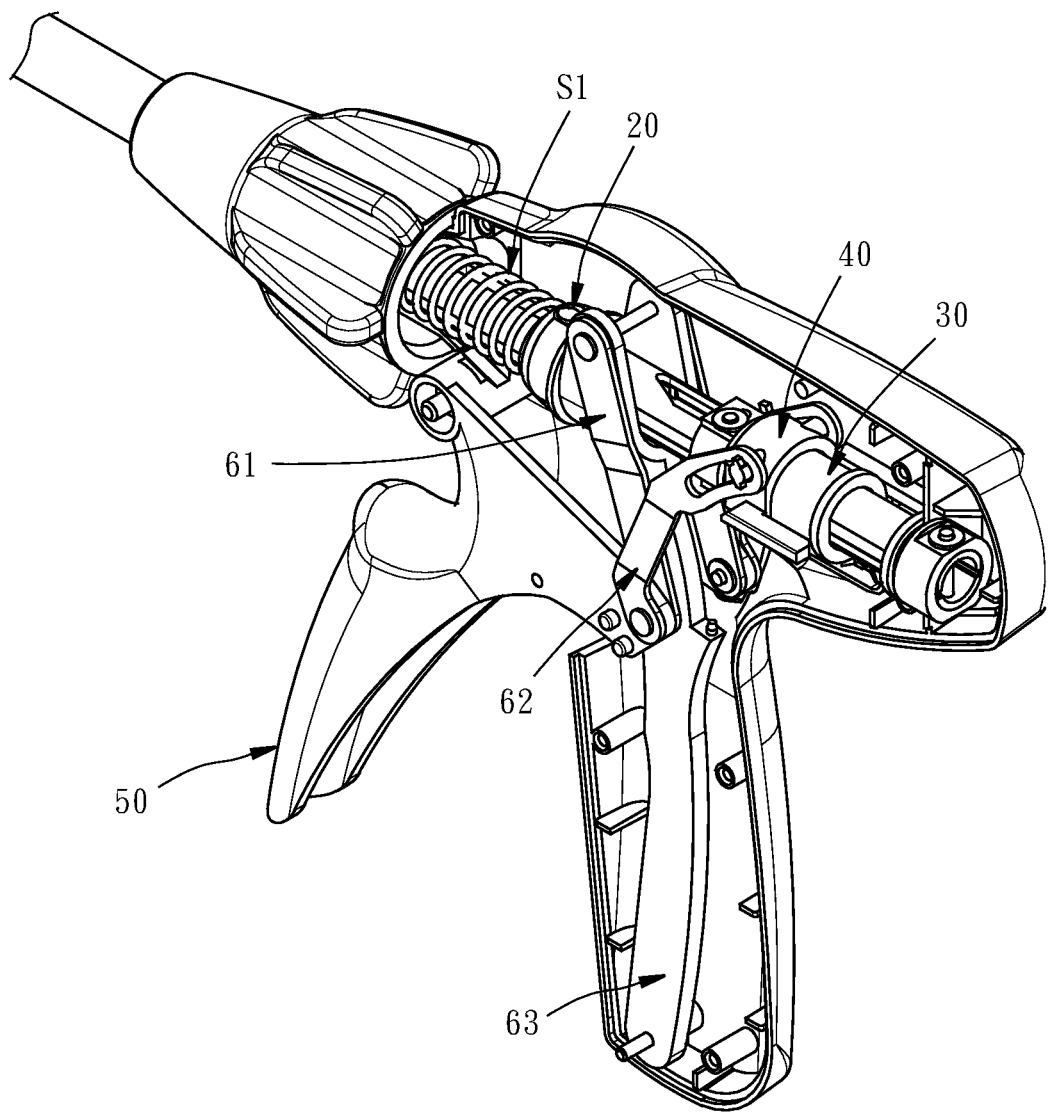
FIG. 10 is a perspective view of the operating structure of a surgical clip applier according to another preferred embodiment of the present invention but with a casing thereof removed.

The operating structure of a surgical clip applier according to another preferred embodiment of the present invention is illustrated by FIG. 10 and described below.

This preferred embodiment is distinguished by the preceding preferred embodiment by the following distinguishing features: the body 1 of the operating structure of a surgical clip applier dispenses with the positioning teeth 171, the oblique protruding portions 172 and the tooth escape recesses 173; and the operating structure of a surgical clip applier dispenses with the tooth positioning element 70 and the counting unit 90. Hence, this preferred embodiment features simplified structures but can still achieve the main objectives of the present invention.

However, the claimed scope of the present invention is not restricted to all the foresaid components but is broadly defined as follows: an operating structure of a surgical clip applier drives a clip clamping unit A. The operating structure of a surgical clip applier comprises:

a body 1;

a front driving element 20 for driving the clip clamping unit A;

a restoring spring S1 for driving the front driving element 20 to move backward;

a press-control element 50 pivotally connected to the body 1;

a front driving arm 61 pivotally connected to the press-control element 50; and a lower driving arm 63 with two ends pivotally connected to the body 1 and the front driving arm 61, respectively, wherein the lower driving arm 63 drives the front driving element 20 to move forward.

Another scope of the claims of the present invention is defined by one or more features of the operating structure of a surgical clip applier according to the present invention, as described below.

For instance, the operating structure of a surgical clip applier further comprises a tooth positioning element 70 pivotally connected to the lower driving arm 63. The tooth positioning element 70 has a resilient arm 71 with dogs 72. A compression spring S2 presses against the lower driving arm 63 and the tooth positioning element 70. The body 1 has positioning teeth 171 whereby the tooth positioning element 70 is positioned in place.

Alternatively, the body 1 has an oblique protruding portion 172 disposed beside the positioning teeth 171 and a tooth escape recess 173 disposed below the positioning teeth 171. The tooth positioning element 70 has a stud 73 which is slided into the tooth escape recess 173 of the body 1 through the oblique protruding portion 172.

Alternatively, the operating structure of a surgical clip applier further comprises: a rear driving element 30 for driving the clip clamping unit A; a rear slider 40 having a slide rod 42 for driving the rear driving element 30; and a rear driving arm 62 pivotally connected to the press-control element 50 and having an oblong hole 621 which the slide rod 42 of the rear slider 40 is penetratingly disposed at to effectuate driving.

Alternatively, the operating structure of a surgical clip applier further comprises: a counting unit 90 having a ratchet wheel 91 which displays numerals; a wheel press-rotating element 92 pivotally disposed at and resiliently pressed against the press-control element 50 once to drive the ratchet wheel 91 to turn by one tooth's angle; and a reverse rotation preventing element 93 for preventing reverse rotation of the ratchet wheel 91.

Alternatively, the body 1 has a spring-pressing portion 13. The restoring spring S1 fits between the front driving element 20 and the spring-pressing portion 13 of the body 1.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An operating structure of a surgical clip applier for driving a clip clamping unit, the operating structure comprising:
    a body;
    a front driving element for driving the clip clamping unit;
    a restoring spring for driving the front driving element to move backward;
    a press-control element pivotally connected to the body;
    a front driving arm pivotally connected to the press-control element;
    a lower driving arm with two ends pivotally connected to the body and the front driving arm, respectively, wherein the lower driving arm drives the front driving element to move forward;
    a tooth positioning element pivotally connected to the lower driving arm, the tooth positioning element having a resilient arm with dogs, wherein a compression spring presses against the lower driving arm and the tooth positioning element, and the body has positioning teeth whereby the tooth positioning element is positioned in place; and
    wherein the body has an oblique protruding portion disposed beside the positioning teeth and a tooth escape recess disposed below the positioning teeth, whereas the tooth positioning element has a stud slidable into the tooth escape recess of the body through the oblique protruding portion.

2. The operating structure of a surgical clip applier according to claim 1, further comprising: a rear driving element for driving the clip clamping unit; a rear slider having a slide rod for driving the rear driving element; and a rear driving arm pivotally connected to the press-control element and having an oblong hole which the slide rod of the rear slider is penetratingly disposed at to effectuate driving.

3. The operating structure of a surgical clip applier according to claim 2, further comprising a counting unit having a ratchet wheel, a wheel press-rotating element, and a reverse rotation preventing element, the ratchet wheel displaying numerals, the wheel press-rotating element being pivotally disposed at and resiliently pressed against the press-control element once to drive the ratchet wheel to turn by one tooth's angle, and the reverse rotation preventing element preventing reverse rotation of the ratchet wheel.

4. The operating structure of a surgical clip applier according to claim 3, wherein the body has a spring-pressing portion, and the restoring spring fits between the front driving element and the spring-pressing portion of the body.

5. The operating structure of a surgical clip applier according to claim 2, wherein the body has a spring-pressing portion, and the restoring spring fits between the front driving element and the spring-pressing portion of the body.

6. The operating structure of a surgical clip applier according to claim 1, further comprising a counting unit having a ratchet wheel, a wheel press-rotating element, and a reverse rotation preventing element, the ratchet wheel displaying numerals, the wheel press-rotating element being pivotally disposed at and resiliently pressed against the press-control element once to drive the ratchet wheel to turn by one tooth's angle, and the reverse rotation preventing element preventing reverse rotation of the ratchet wheel.

7. The operating structure of a surgical clip applier according to claim 6, wherein the body has a spring-pressing portion, and the restoring spring fits between the front driving element and the spring-pressing portion of the body.

8. The operating structure of a surgical clip applier according to claim 1, wherein the body has a spring-pressing portion, and the restoring spring fits between the front driving element and the spring-pressing portion of the body.

* * * * *